(12) United States Patent
Kiyama et al.

(10) Patent No.: US 11,441,114 B2
(45) Date of Patent: Sep. 13, 2022

(54) LIQUID FEED DEVICE, AND CELL CULTURE DEVICE AND METHOD USING SAME

(71) Applicant: Hitachi, Ltd., Tokyo (JP)

(72) Inventors: Masaharu Kiyama, Tokyo (JP); Guangbin Zhou, Tokyo (JP); Daisuke Suzuki, Tokyo (JP); Midori Kato, Tokyo (JP); Hikaru Saito, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 469 days.

(21) Appl. No.: 16/316,908

(22) PCT Filed: Feb. 24, 2017

(86) PCT No.: PCT/JP2017/007098
§ 371 (c)(1),
(2) Date: Jan. 10, 2019

(87) PCT Pub. No.: WO2018/042710
PCT Pub. Date: Mar. 8, 2018

(65) Prior Publication Data
US 2019/0300837 A1 Oct. 3, 2019

(30) Foreign Application Priority Data
Aug. 29, 2016 (JP) .............................. JP2016-166681

(51) Int. Cl.
*C12M 1/12* (2006.01)
*C12M 1/00* (2006.01)
(Continued)

(52) U.S. Cl.
CPC .............. *C12M 37/00* (2013.01); *C12M 1/00* (2013.01); *C12M 29/06* (2013.01); *C12M 41/12* (2013.01); *C12M 41/48* (2013.01)

(58) Field of Classification Search
CPC ........ C12M 37/00; C12M 1/00; C12M 29/06; C12M 41/12; C12M 41/48
See application file for complete search history.

(56) References Cited

U.S. PATENT DOCUMENTS 4,889,812 A * 12/1989 Guinn .................... C12M 29/12
435/286.7
2006/0115889 A1 6/2006 Nakashima et al.
(Continued)

FOREIGN PATENT DOCUMENTS

JP 2006-149268 A 6/2006
JP 2007-222120 A 9/2007
(Continued)

OTHER PUBLICATIONS

International Search Report (PCT/ISA/210) issued in PCT Application No. PCT/JP2017/007098 dated May 30, 2017 with English translation (five (5) pages).
(Continued)

*Primary Examiner* — William H. Beisner
*Assistant Examiner* — Danielle B Henkel
(74) *Attorney, Agent, or Firm* — Crowell & Moring LLP

(57) ABSTRACT

A liquid feed device that feeds a liquid medium and a cell suspension to target containers by respectively suited liquid feed methods is provided. A pump 6 is connected between a first liquid bottle 12 containing a liquid medium and a second liquid bottle 2 containing a cell suspension, and a receptacle 8 to be used as a culture container is connected downstream of a second liquid bottle 12. The liquid medium in the first liquid bottle is sent to the receptacle through the pump 6 and a branch point 20 by opening a first supply valve 17, and the cell suspension in the second liquid bottle is sent to the receptacle by opening a first gas introducing valve 10, a second gas introducing valve 15, and a second supply valve 19 and transferring, by pressure, a gas supplied from
(Continued)

the first gas introducing valve 10 to the second liquid bottle through the pump 6 and a branch point 16.

11 Claims, 9 Drawing Sheets

(51) Int. Cl.
*C12M 1/34* (2006.01)
*C12M 1/36* (2006.01)

(56) References Cited

U.S. PATENT DOCUMENTS

| | | | |
|---|---|---|---|
| 2010/0317102 A1* | 12/2010 | Suzuki | C12N 5/0602 435/303.1 |
| 2014/0335608 A1 | 11/2014 | Tanaka et al. | |
| 2015/0247114 A1* | 9/2015 | Gebauer | F04B 53/20 435/243 |
| 2016/0108350 A1* | 4/2016 | Kiyama | C12M 41/30 435/303.1 |
| 2017/0198249 A1 | 7/2017 | Kiyama et al. | |
| 2017/0253847 A1 | 9/2017 | Koseki et al. | |
| 2017/0306279 A1* | 10/2017 | Kagawa | C12M 47/04 |

FOREIGN PATENT DOCUMENTS

| | | |
|---|---|---|
| JP | 2008-253154 A | 10/2008 |
| JP | 2015-123012 A | 7/2015 |
| JP | 2015-188381 A | 11/2015 |
| JP | 2016-59316 A | 4/2016 |
| WO | WO 2013/114845 A1 | 8/2013 |
| WO | WO 2015/025425 A1 | 2/2015 |
| WO | WO-2015025425 A1 * | 2/2015 ............ C12M 41/34 |
| WO | WO 2016/013070 A1 | 1/2016 |

OTHER PUBLICATIONS

Japanese-language Written Opinion (PCT/ISA/237) issued in PCT Application No. PCT/JP2017/007098 dated May 30, 2017 (six (6) pages).

* cited by examiner

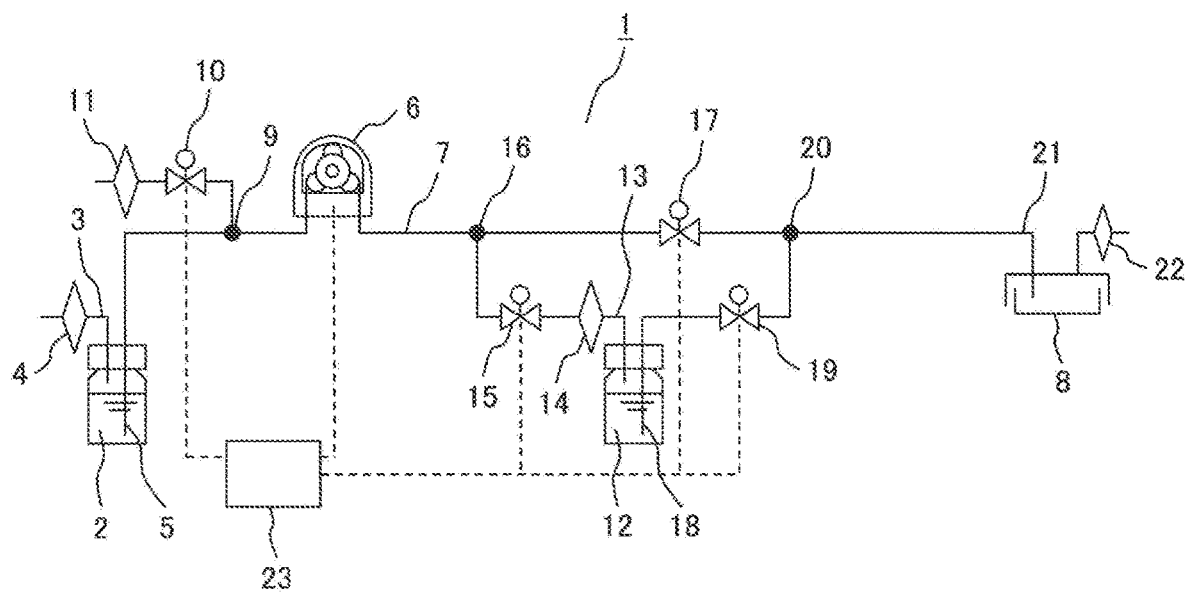

FIG. 7

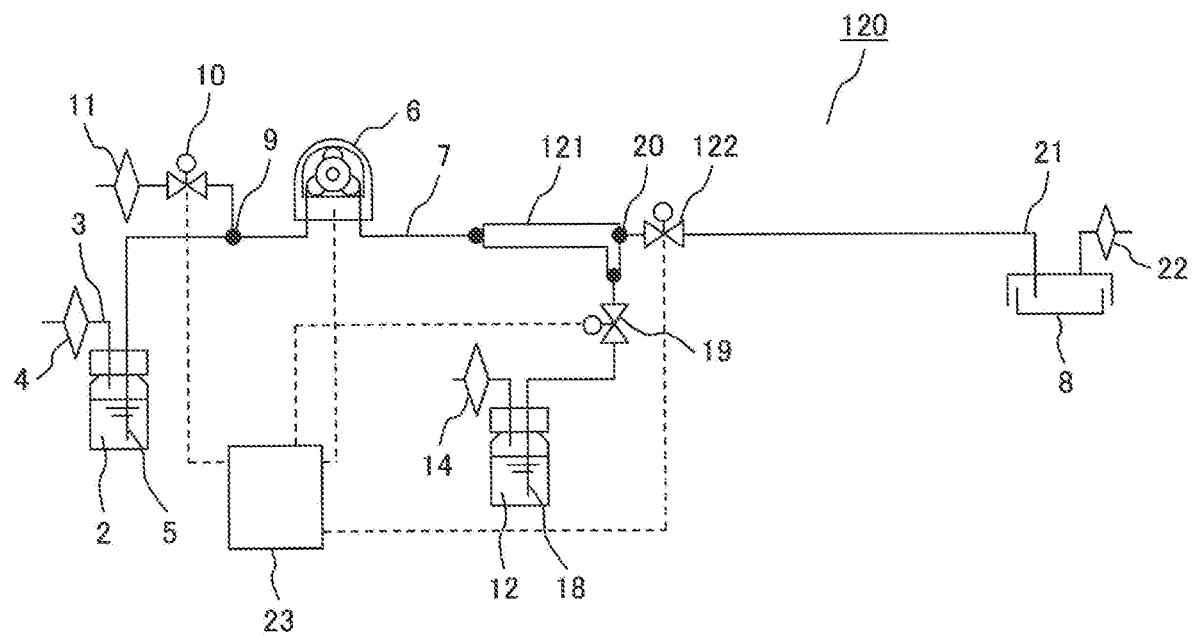

LIQUID FEED DEVICE, AND CELL CULTURE DEVICE AND METHOD USING SAME

TECHNICAL FIELD

The present invention relates to a cell culture device and method to culture cells, and in particular relates to a liquid feed technique therefor.

BACKGROUND ART

In regenerative medicine to treat diseases using cells of a patient him/herself or cells of another individual, cells collected from a living body are cultured to be increased in number or tissue is structured into a desired form to be used for a transplantation therapy. Culturing of cells used in treatment has to be performed in a clean room for cell culture called a cell processing center (Cell Processing Center: CPC) and conforming to GMPs (Good Manufacturing Practices). Because cell culturing is performed by manual work of engineers, there are problems here that it takes much labor and cost and that there is a risk of biological contamination because it is performed manually.

As means for solving such problems of manual work, devices to automate cell culture processes in closed systems have been developed. They achieve automation of cell culture processes and lowering of the risk of biological contamination by using closed system culture containers that do not require manipulation of opening and closing lids of the culture containers. There is a method for an automatic culture device in which dispensers are mechanized and liquid addition is performed in operations performed in an interlocking manner for preparative isolation and transfer similar to manual manipulation, but the device is increased in size because it is necessary to install the entire device in a sterile environment. On the other hand, there is a method of simultaneously performing quantitative determination and liquid feeding using a pump by connecting spaces from a liquid bottle to a culture plate using a disposable tube if the pump is used for dispensing operation. In this case, it is only needed to maintain the inside of the tube through which a liquid is fed in a sterile state, and an automated device can be downsized. PTL 1 mentioned below discloses an automatic culture device in which a mechanized dispenser is used, and PTL 2 discloses an automatic culture device in which pump liquid feed is used.

CITATION LIST

Patent Literature

PTL 1: Japanese Patent Application Laid-Open No. 2006-149268
PTL 2: Japanese Patent Application Laid-Open No. 2007-222120

SUMMARY OF INVENTION

Technical Problem

Beginning with PTL 2, generally if a pump is used for dispensing, methods to cause liquids to flow in one direction are used, in which a bottle containing a liquid medium to be the source of liquid feed or a liquid medium in which cells or a biological sample are suspended (hereinafter, referred to as a cell suspension) is arranged upstream of the pump, and a container such as a culture plate is arranged downstream of the pump. At this time, if the cell suspension passes through the inside of the pump, there is a concern in some cases that an excessive load occurs to the cells or biological sample after the passage due to a pressure change accompanying liquid feed.

An object of the present invention is to solve such problems and to provide a liquid feed device that reduces the stress load on cells or biological samples contained in a liquid at the time of liquid feed, and a cell culture device and method using the same.

Solution to Problem

In order to achieve the abovementioned objects, the present invention provides a liquid feed device configured to include: a first liquid containing unit that contains a first liquid; a second liquid containing unit that contains a second liquid; a pump connected between the first liquid containing unit and the second liquid containing unit; a receptacle connected downstream of the second liquid containing unit; a first supply pipe that supplies the first liquid to the receptacle through the pump; and a second supply pipe that supplies the second liquid to the receptacle.

In addition, in order to achieve the abovementioned objects, the present invention provide a cell culture device configured to include: a thermostat; a culture container arranged in the thermostat; a liquid feed device that feeds and discharges a liquid to and from the culture container; and a control unit that controls the thermostat and the liquid feed device, wherein the liquid feed device has: a first liquid containing unit that contains a first liquid; a second liquid containing unit that contains a second liquid; a pump connected between the first liquid containing unit and the second liquid containing unit; a first supply pipe that supplies the first liquid to the culture container through the pump; and a second supply pipe that supplies the second liquid to the culture container.

Furthermore, in order to achieve the abovementioned objects, the present invention provides a cell culture method that performs cell culture using, as a liquid feed device that feeds and discharges a liquid to and from a culture container arranged in a thermostat, a liquid feed device with a configuration having: a first liquid containing unit that contains a first liquid; a second liquid containing unit that contains a second liquid; a pump connected between the first liquid containing unit and the second liquid containing unit; a first supply pipe that supplies the first liquid to the culture container through the pump; and a second supply pipe that supplies the second liquid to the culture container.

Advantageous Effects of Invention

According to the present invention, the stress load on cells or biological samples contained in a liquid at the time of liquid feed can be reduced.

BRIEF DESCRIPTION OF DRAWINGS

FIG. 1 is a figure of one configuration of a liquid feed device in Example 1.
FIG. 2 is a figure showing one example of a control time chart about the liquid feed device in Example 1.

FIG. 7 is a figure showing a control time chart example of the automatic culture device in Example 1.

FIG. 10 is a figure of one configuration of a liquid feed device in Example 3.

FIG. 11 is a figure showing a control flowchart example about the liquid feed device in Example 3.

DESCRIPTION OF EMBODIMENTS

Figure 3:
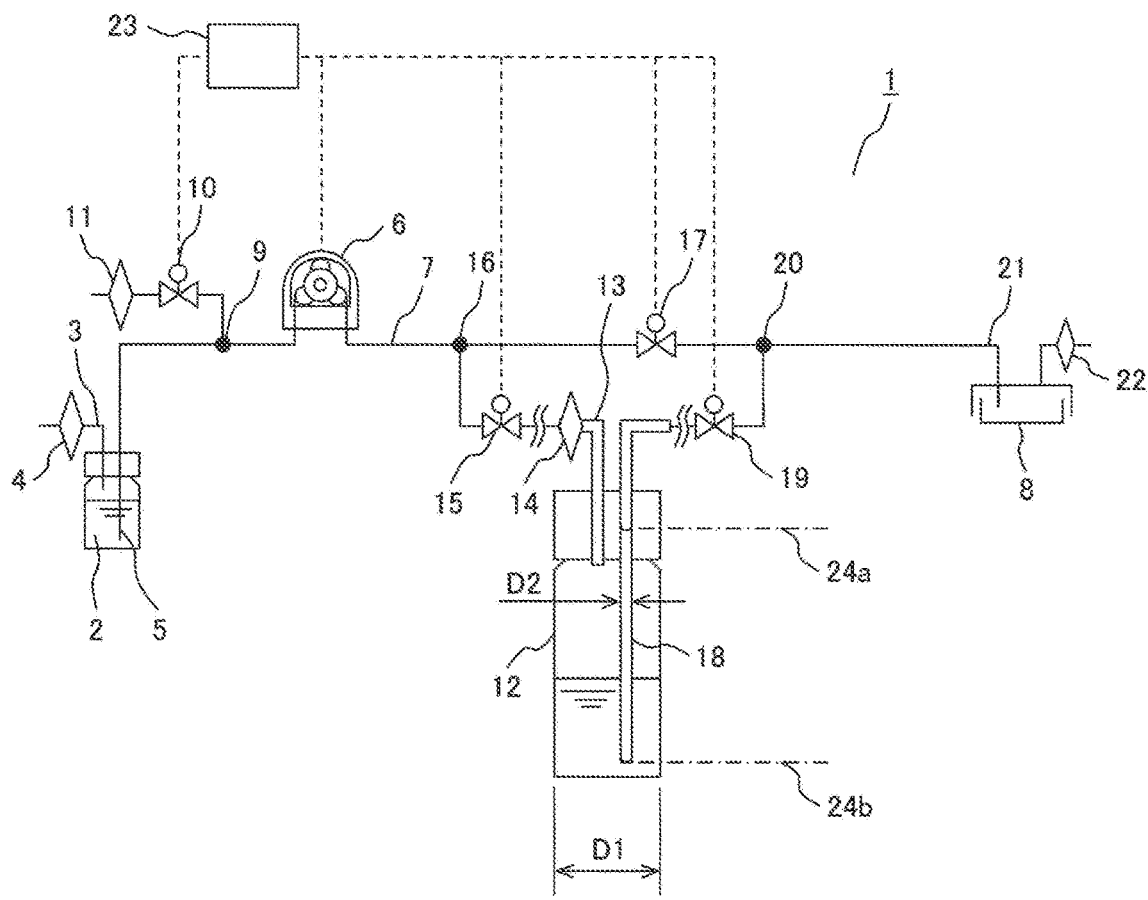
FIG. 3 is a figure of another configuration of the liquid feed device in Example 1.

Hereinafter, various examples of the present invention are explained with reference to the attached drawings. However, these examples are merely one example for realizing the present invention, and not to limit the technical scope of the present invention. In addition, the same reference numbers are given to common configurations in the respective figures. Note that in the present specification, liquid feed pipes to feed liquids and gas feed pipes to feed gases are collectively called supply pipes, and these supply pipes function as liquid feed pipes or gas feed pipes.

Example 1

Example 1 is an example of: a liquid feed device configured to include: a first liquid containing unit that contains a first liquid; a second liquid containing unit that contains a second liquid; a pump connected between the first liquid containing unit and the second liquid containing unit; a receptacle connected downstream of the second liquid containing unit; a first supply pipe that supplies the first liquid to the receptacle through the pump; and a second supply pipe that supplies the second liquid to the receptacle; and a cell culture device using the liquid feed device. Hereinafter, the liquid feed device and the cell culture device using it according to Example 1 are explained with reference to FIG. 1 to FIG. 7. They are explained in the following order: the configurations of the liquid feed device, a cell culture container and an automatic cell culture device; and manipulation of cell culture.

<Liquid Feed Device>

FIG. 1 is a figure showing one configuration of the liquid feed device in the first example. In a liquid feed device 1, a first liquid bottle 2 which is a first liquid containing unit to contain a liquid can keep its inner space airtightly with its lid (lid). A gas pressure adjusting pipeline 3 for gas pressure adjustment provided to the lid is open to the external air through a filter 4 provided to an open end thereof and having a mesh size of 0.22 μm. A supply pipe 5 provided to the lid has an open end inside the first liquid bottle 2, which serves as a liquid discharge port in contact with the liquid in the liquid bottle 2. One end of a pump 6 is connected to the other end of the supply pipe 5, and the other end of the pump 6 is connected to a supply pipe 7. Note that if the pump 6 is a roller pump or the like, the supply pipe 5 and supply pipe 7 are constituted by one rubber tube, for example, and its flow path is connected to a fluid drive unit of the pump 6. A liquid feed destination of liquid feed of this supply pipe 7 is a liquid supply pipe 21 to supply a receptacle 8 with a liquid. The supply pipe 5 and supply pipe 7 are collectively called a first supply pipe in some cases.

A branch point 9 is provided above the liquid surface of the liquid in the first liquid bottle contained in the first liquid bottle 2 of the supply pipe 5. This is for, as explained below, causing a liquid in the supply pipe 5 between the position of the branch point 9 and the first liquid bottle 2 to return to the liquid bottle 2 by means of the potential energy generated due to a difference in elevation of the liquid when a first gas introducing valve 10 is opened and a gas is fed. This is because if a liquid is kept contained in the supply pipe 5, clogging occurs when the liquid dries, and this should be prevented.

The first gas introducing valve 10 opens and closes a pipe connected to the branch point 9 and a filter 11. A valve mechanism used for this first gas introducing valve 10 is suitably a solenoid valve. A so-called solenoid valve has a mechanism in which a rubber tube is attached to and sandwiched by a part that opens and closes due to an effect of an electromagnet, and a pipe portion is opened and closed by elastically deforming the rubber tube according to turning on/off of the solenoid valve. Hereinafter, in the present specification, elements referred to as valves means solenoid valves. The filter 11 is a filter having a mesh size of 0.22 μm and is in contact with the external air.

A second liquid bottle 12 which is a second liquid containing unit to contain a liquid keeps its inner space airtightly with a lid. The second liquid bottle 12 is connected to a second gas introducing valve 15 via a filter 14 having a mesh size of 0.22 μm and provided to an open end of a gas pressure adjusting pipeline 13 which is a gas pipeline 13 provided to the lid. The gas pipeline 13 reaches a branch 16 through the second gas introducing valve 15. The first gas introducing valve 10 and second gas introducing valve 15 constitute a gas introducing valve that introduces a gas into the second liquid bottle 12 which is the second liquid containing unit. A branch point 16 is provided at an intermediate position of the supply pipe 7 extending from one end of the pump 6, and the abovementioned gas pipeline 13 branches off at the branch point 16. The gas pipeline 13 is opened and closed by the second gas introducing valve 15, and the supply pipe 7 is opened and closed by a first supply valve 17 inserted between the branch point 16 and a branch point 20.

A supply pipe 18 provided to the lid of the second liquid bottle 12 has an open end inside the second liquid bottle 12, which serves as a liquid discharge port in contact with a liquid. Note that this supply pipe 18 may be called a second supply pipe. A second supply valve 19 is connected at an intermediate position of the supply pipe 18, and the second supply valve 19 opens and closes the supply pipe 18. The branch point 20 of the supply pipe 7 and the supply pipe 18 is connected to the liquid supply pipe 21 to the receptacle 8 closed off by a highly airtight lid. Note that the receptacle 8 is provided with a filter 22 for gas pressure adjustment. An open portion of this liquid supply pipe 21 and the branch point 20 are provided above the liquid surface of the liquid in the second liquid bottle 12. This is for causing the liquid to return to the second liquid bottle 12 to prevent clogging. In such pressurized liquid feed from the second liquid bottle 12, installation of the open portion of the liquid supply pipe 21 and the branch point 20 above the liquid surface in the second liquid bottle 12 prevents a liquid in the pipe from not returning therefrom but remaining therein.

Opening and closure of the abovementioned pump 6, first gas introducing valve 10, second gas introducing valve 15, first supply valve 17 and second supply valve 19, that is, operation of opening and closure thereof is controlled by a controller 23 which is a control unit. The controller 23 can be realized by execution of a program by a central processing unit (CPU).

The liquid feed device 1 performs feeding of a liquid in the first liquid bottle 2 in the following manner. The flow rate of the pump 6 is assumed to be approximately Q. If the first gas introducing valve 10, second gas introducing valve 15 and second supply valve 19 are closed, and the first supply valve 17 is opened, and then the pump 6 is activated, the pump 6 feeds a gas in the supply pipe 5, the liquid in the first liquid bottle 2 continuous with the gas passes the supply pipe 5 and liquid feed is thus started. The liquid passes the branch point 9, and upon completion of supply of a predetermined liquid volume A from the first liquid bottle 2, the pump 6 is stopped. When the pump 6 is stopped, the pipe is blocked due to the internal structure of the pump 6, and the liquid does not move.

Next, if the first gas introducing valve 10 is opened, a gas is introduced through the filter 11, and additionally a liquid (return volume B) which is in the supply pipe 5 on the first liquid bottle 2 side relative to the position of the branch point 9 returns to the liquid bottle 2 due to the energy resulting from a difference in elevation. A liquid on the pump 6 side relative to the branch point 9 maintains its stopped state due to the abovementioned internal structure of the pump 6. This liquid on the pump 6 side becomes a target predetermined liquid feed volume. Next, if the pump 6 is actuated for a predetermined length of time, a gas is sequentially introduced through the filter 11, and additionally a liquid moves through the supply pipe 7 toward the liquid supply pipe 21. The front end of the liquid arrives at the receptacle 8, addition of the liquid is started thereby, and if the rear end of the liquid arrives at the receptacle 8, the pump 6 is stopped.

Next, the liquid feed device 1 performs feeding of a liquid in the second liquid bottle 12 in the following manner. If the first supply valve 17 is closed, the first gas introducing valve 10, second gas introducing valve 15 and second supply valve 19 are opened, and then the pump 6 is activated, a gas is introduced through the filter 11, and additionally the pump 6 starts pressurization through the branch point 9 on the liquid in the second liquid bottle 12. Due to pressure propagation through the gas phase, the liquid in the second liquid bottle 12 passes the second supply valve 19 through the supply pipe 18, and liquid feed to the receptacle 8 is started thereby. The liquid passes the branch point 20, upon completion of supply of a predetermined liquid volume C from the second liquid bottle 12, the pump 6 is stopped, and additionally the second gas introducing valve 15 and second supply valve 19 are closed. Due to the action of the respective valves, the supply pipe 18 is blocked, and a liquid does not move therethrough. At this time, the pipe upstream of the branch point 20 in the supply pipe 18 is filled with a liquid, and the liquid volume equivalent to the inner volume of the pipe determined by the length and diameter of the pipe is assumed to be D.

Next, if the first supply valve 17 is opened and the pump 6 is activated, a gas is introduced through the filter 11, and the gas moves through the branch point 16 and first supply valve 17 to move a liquid downstream of the position of the branch point 20 on the container side to the receptacle 8. The front end of the liquid arrives at the receptacle 8, addition of the liquid is started thereby, and if the rear end of the liquid arrives at the receptacle 8, the pump 6 is stopped.

FIG. 2 shows one example of a control time chart about the liquid feed device of the present example. At the time of first liquid addition, that is, at the time of feeding of a first liquid, the first supply valve 17 is opened at "START", then the pump 6 is activated, and the liquid feed is started thereby. Upon completion of supply of the predetermined liquid volume A from the first liquid bottle 2, activation of the pump 6 is promptly stopped. Next, the first gas introducing valve 10 is opened. A length of time which is longer than that required for the rear end of the liquid to arrive at the receptacle 8 is set as the length of time during which the pump 6 is activated, and the pump 6 is activated for the length of time. After the given length of time, the pump 6 is stopped, and then all the valves are closed.

Next, at the time of second liquid addition, that is, at the time of feeding of a second liquid, the first gas introducing valve 10, second gas introducing valve 15 and second supply valve 19 are opened, then the pump 6 is activated, and the liquid feed is started thereby. Upon completion of supply of the predetermined liquid volume C from the first liquid bottle 2, activation of the pump 6 is promptly stopped. Next, the second supply valve 19 and second gas introducing valve 15 are closed, and then the first supply valve 17 is opened. A length of time longer than that required for the rear end of the liquid to arrive at the receptacle 8 is set for the pump 6, and the pump 6 is activated for the length of time. After the given length of the time, the pump 6 is stopped. Thereafter, the second gas introducing valve 15 is opened, and then all the valves are closed.

The timing of opening and closure of each valve after completion of supply of the predetermined liquid volume C from the first liquid bottle 2 and after activation of the pump 6 is once stopped is important for feeding a liquid accurately. To first close the second supply valve 19 and second gas introducing valve 15 and stop the flows of a liquid and a gas keeps an increased pressure in the second liquid bottle 12 within the bottle 2, and by opening the second gas introducing valve 15 after the rear end of the liquid arrives at the receptacle 8, the gas phase pressure in the bottle is propagated to the container 8 side through the first supply valve 17, and this results in the pressure to be applied onto the liquid in the pipe being maintained at the normal pressure.

By using the liquid feed device 1 of the present example explained above, a liquid that is desired to avoid as much as possible influence of pressure changes in the liquid to be the source of liquid feed is contained in the second liquid bottle 12, and a liquid that is less susceptible to influence of pressure changes in the liquid to be the source of liquid feed is contained in the first liquid bottle 2; thereby, the liquid that is desired to avoid as much as possible influence of pressure changes can be fed to a target container with reduced influence of passing though the pump 6; on the other hand, the liquid that is not susceptible to influence of pressure changes can pass the pump 6, and be fed to a target container quantitatively repetitively.

A reason for this is because the liquid that is desired to avoid as much as possible influence of pressure changes is contained in the second liquid bottle 12 arranged downstream of the pump 6 and is fed to the target container 8 by pressure propagation via a gas phase; thereby, it can be fed to the target container with reduced influence of passing the inside of the pump 6. In addition, on the other hand, the liquid that is not susceptible to influence of pressure changes is contained in the first liquid bottle 2 arranged upstream of the pump 6, and fed by passing the pump 6; as a result, it can be fed to the target container repetitively by quantitative control according to the flow rate accuracy of the pump 6.

At this time, if a suspension of cells or a biological sample is contained in the second liquid bottle 12, the suspension of cells or the like can be fed to the receptacle without passing the pump, and the load on the cells or biological sample can be reduced. In addition, if a liquid medium or the like is contained in the first liquid bottle 2, the liquid medium can be fed quantitatively repetitively. The pump 6 is suitably a roller pump, but another form of pump such as a diaphragm pump or a gear pump can also be applied as the pump 6. A roller pump, which is a so-called peristaltic pump or tube pump has a mechanism in which a rubber tube is wound around a roller attached to a motor rotational shaft and rotation of the motor elastically deforms the rubber tube to feed a gas or liquid therein. It is necessary to ensure sterility of a tube for liquid feeding in a cell culture device, and a roller pump which allows replacement of a tube at the time of use is useful. If internal sterilization is possible before use, any type of liquid feed pump can be used.

In addition, a configuration to not move a liquid inside is necessary at the time of stopping the pump, but by configuring a pipeline via a check valve that limits a flow toward a liquid feed bottle side before or after the pump at the time of use of the pump during which a liquid moves, it can be applied to the device of the present example.

Although in the flowchart example shown in FIG. 2, for convenience of explanation, it is explained that the first liquid is fed first, and next the second liquid is fed later, the order in which the first or second liquid is fed first or later can be reversed.

About the liquid feed device of the present example explained above, in repetitively feeding a liquid in the second liquid bottle 12, the liquid surface of the liquid at the first time is inside the second liquid bottle 12, but the liquid surface at the time of next liquid feed is at the position of the branch point 20 in the supply pipe 18. The liquid volume is, as mentioned above, the volume D equivalent to the inner volume of the pipe upstream of the branch point 20 in the supply pipe 18, but at the time of first liquid feed, liquid feed control may be performed taking into consideration the difference volume. In addition, at the second and latter liquid feed, as long as there is a certain volume of liquid contained in the second liquid bottle 12, an end portion of the liquid surface is always positioned at the branch point 20; therefore, in implementing liquid feed multiple times, it is possible to perform highly accurate liquid feed by performing control on the pump to feed a constant volume of liquid.

On the other hand, with the liquid feed device of the present example, it is also possible to perform liquid feed after stirring a liquid to be fed by another liquid feed method. The configuration of a liquid feed device in FIG. 3 is the same as the configuration in the example shown in FIG. 1, and configuration parts related to the second liquid bottle 12 are illustrated in detail.

In the figure, at the time of feeding of the second liquid, if the first gas introducing valve 10, second gas introducing valve 15 and second supply valve 19 are opened, and then the pump 6 is activated, a gas is introduced through the filter 10, and additionally the pump 6 starts pressurization through the branch point 16 and branch point 16 on a liquid in the second liquid bottle 12. When given liquid feed is performed, the second liquid in the supply pipe advances to the liquid surface 24a position. Next, if the pump 6 is activated under a suction condition opposite to the normal suction condition, the inside of the second liquid bottle 12 is brought to a negative pressure, the second liquid contained in the supply pipe 18 returns to a liquid in the second liquid bottle 12, and the liquid flow stirs the liquid in the second liquid bottle 12.

By repetitively performing these pressurization and suction operations, a liquid can be stirred highly efficiently. This is pronounced if a liquid feed target is a liquid in which a liquid composition is not uniform, and for example in a case of a cell suspension in which cells are suspended in a medium, a manual stirring operation is performed by generating a convection current in the liquid by pushing and pulling a piston of a dispenser before cell seeding. With the liquid feed device of the present example, if seeding is performed in a plurality of culture containers as receptacles, stirring of a liquid can be realized by operations of pressurization and suction by driving of the pump before liquid feed.

Next, a reason why reproducibility can be ensured although a liquid being fed is stirred is explained in the following method. After the abovementioned stirring manipulation, and immediately before feeding of the second liquid, the pump 6 is activated under a suction condition which is slightly longer than a pressurization condition and then stopped; thereby, a gas is introduced through the supply pipe 18 through the filter 22 provided to the receptacle 8, and gas supply in the second liquid bottle 12 is performed. At this time, if a sufficient length of time during which the flow of a gas is stopped is given, a liquid surface 24b to be a liquid feed start point is at the position of an open end of the supply pipe 18 inside the second liquid bottle 12. Thereafter, if the abovementioned liquid feed procedure, pressurization procedure, and suction procedure under a suction condition which is slightly longer than a pressurization condition are performed, and the abovementioned stirring and the liquid feed procedure are repetitively performed before the next liquid feed, the liquid feed start point always stays constant. Liquid feed with good reproducibility requiring simpler liquid feed control is possible. This effect is pronounced if a liquid feed target is quantitatively fed to a plurality of culture containers, and even if the liquid volume contained in a liquid bottle is reduced due to liquid feed manipulation, the liquid surface to be a starting point of liquid feed can be controlled to always stay at a constant position; as a result, liquid feed control can be realized by temporal control based on a flow rate of the pump and a target liquid volume such that a liquid with the target liquid volume passes a space equivalent to the pipe volume estimated from the length and diameter of a pipe to a target container.

Figure 4:
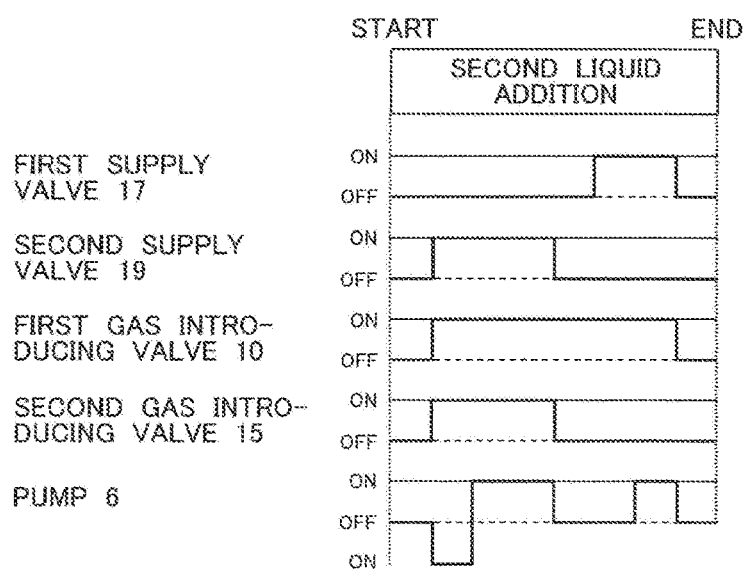
FIG. 4 is a figure showing another example of a control time chart about the liquid feed device in Example 1.

FIG. 4 shows a control flowchart of a method of feeding a liquid after being stirred while ensuring reproducibility of liquid feeding in Example 1. At the time of feeding of the first liquid, as explained with reference to FIG. 2, the first supply valve 17 is opened at "START", then the pump 6 is activated, and the feeding of the first liquid is started thereby. Upon completion of supply of the predetermined liquid volume A from the first liquid bottle 2, activation of the pump 6 is promptly stopped. Next, the first gas introducing valve 10 is opened. A length of time which is longer than that required for the rear end of the liquid to arrive at the receptacle 8 is set as the length of time during which the pump 6 is activated, and the pump 6 is operated for the length of time. After the given length of time, the pump 6 is stopped, and then all the valves are closed.

Next, at the time of feeding of the second liquid, the first gas introducing valve 10, second gas introducing valve 15 and second supply valve 19 are opened, and then the pump 6 is activated. As shown in FIG. 4, first the pump 6 is activated under a suction condition opposite to the normal suction condition, the inside of the second liquid bottle 12 is brought to a negative pressure, and a liquid in the second liquid bottle 12 is stirred. Thereafter, the pump 6 is activated under the normal condition, and liquid feed is started thereby. Upon completion of supply of the predetermined liquid volume C from the second liquid bottle 12, activation of the pump 6 is promptly stopped. Next, the supply valve 19 and second gas introducing valve 15 are closed, and then the first supply valve 17 is opened. A length of time longer than that required for the rear end of the liquid to arrive at the receptacle 8 is set for the pump 6, and the pump 6 is activated for the length of time. After the given length of the time, the pump 6 is stopped, and then all the valves are closed. Here, similar to FIG. 2, after once second gas introducing valve 15 is opened, all the valves may be closed.

However, because excessive stirring generates load on cells or the like in some cases, in the configuration of the present example, in addition to a condition about the speed of liquid feed inside a pipe, the criterion of the amount of speed change from a container having a larger diameter to a pipe having a small diameter is desirably 10,000% or smaller. That is, the ratio of the diameter D1 of a liquid bottle to the diameter D2 of a supply pipe is recommended to be 1,000% or smaller.

The shape of a liquid bottle is generally cylindrical. It is normally manufactured to have an inner diameter which is smaller at the bottom surface than at the opening, and in addition, the bottom surface portion more preferably has a triangular pyramid shape. By adopting a triangular pyramid shape, that is, a cone-like shape so as to arrange the supply pipe closer to the bottom portion, the remaining volume at the time of discharge from the liquid bottle to the supply pipe can be reduced.

<Configurations of Cell Culture Container and Automatic Cell Culture Device>

Figure 5:
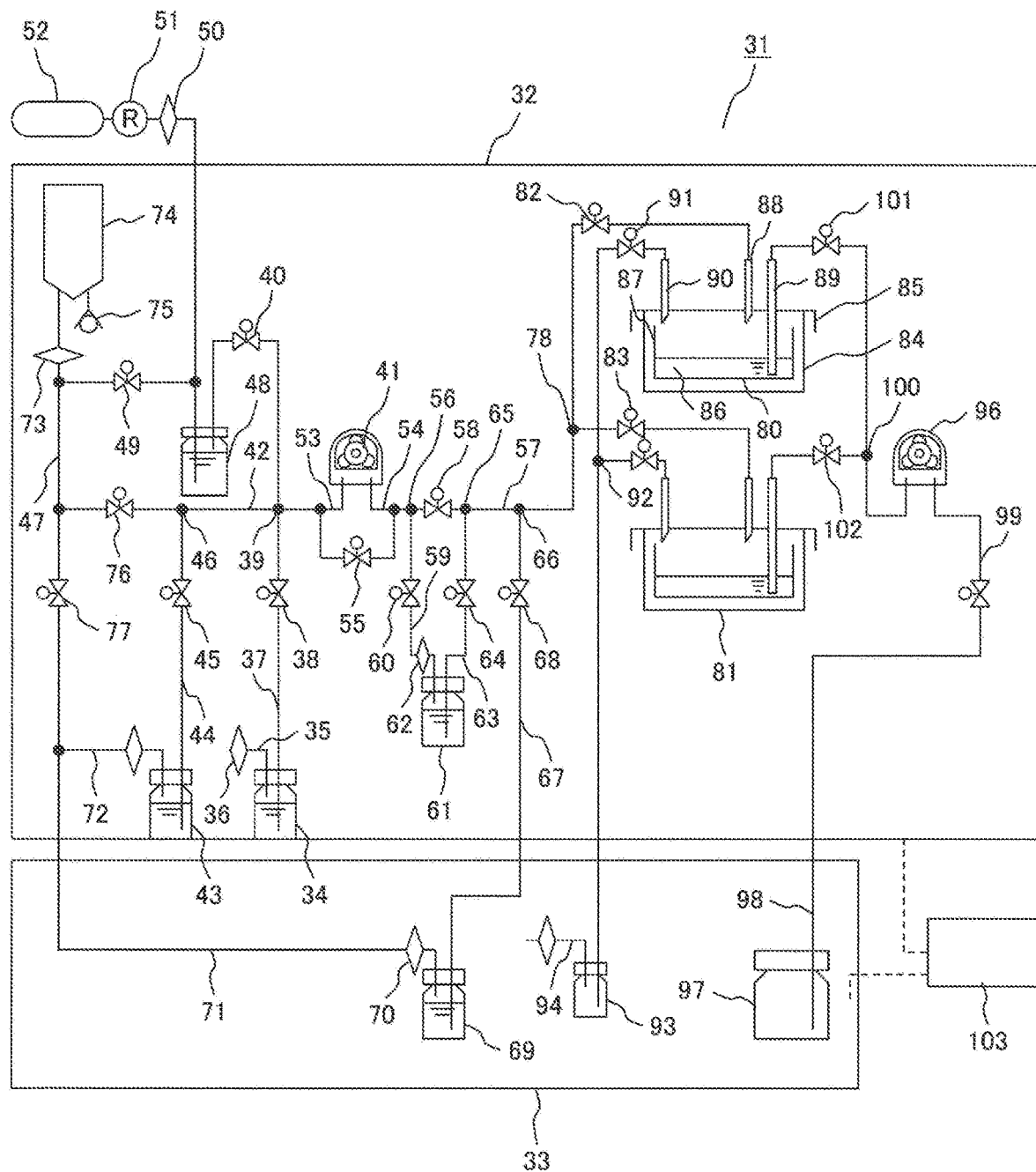
FIG. 5 is a figure of one configuration of the liquid feed device and a cell culture device in Example 1.

FIG. 5 is a figure showing one configuration example of an automatic cell culture device 31 using the liquid feed device 1 of Example 1. The cell culture device of the present example has a configuration having: a thermostat; a culture container arranged in the thermostat; a liquid feed device that feeds and discharges a liquid to and from the culture container; and a control unit that controls the thermostat and the liquid feed device, wherein the liquid feed device has: a first liquid containing unit that contains a first liquid; a second liquid containing unit that contains a second liquid; a pump connected between the first liquid containing unit and the second liquid containing unit; a first supply pipe that supplies the first liquid to the culture container through the pump; a second supply pipe that supplies the second liquid to the culture container; and a gas introducing valve that introduces a gas into the second liquid containing unit, and the present example relates to a cell culture method using the cell culture device.

Hereinafter, an example of the automatic cell culture device including a control unit that performs control to supply or discharge a liquid medium to a cell culture container as a receptacle is explained. A thermostat 32 contains cell culture containers such as a first culture container 80 or a second culture container at a culture temperature optimal for cell culture. A refrigerator 33 contains elements such as a replenishment bottle 69 that are required to be kept at a low temperature.

A first medium bottle 34 which is a first liquid containing unit to contain a seeding medium can keep its inner space airtightly with its lid. The first medium bottle 34 is provided with a gas pressure adjusting pipe 35 for gas pressure adjustment that is provided to one of lids. In addition, a filter 36 with a mesh size of 0.22 μm provided to an open end is installed and open to a gas phase of the thermostat 32. One end of a supply pipe 37 that is provided to the lid and is to function as a first supply pipe has an open end inside the first medium bottle 34, contacts the seeding medium and serves as a liquid discharge port. A first control valve 38 controls a flow in the supply pipe 37. The supply pipe 37 is connected to a common pipe 42 mentioned below via a branch point 39. The branch point 39 is provided above the liquid surface of a liquid contained in the first medium bottle 34.

The configuration of a second medium bottle 43 that contains a replacement medium is similar to the first medium bottle. One end of a supply pipe 44 has an open end inside the second medium bottle 43, contacts the replacement medium, and serves as a liquid discharge port. A second control valve 45 controls a flow in the supply pipe 44. The supply pipe 44 is connected to the common pipe 42 via a branch point 46. The upstream of the common pipe 42 is connected to a first gas pressure adjusting valve 76, and the first gas pressure adjusting valve 76 is connected to a gas common pipe 47 mentioned below. A pump 41 is connected to the downstream of the common pipe 42, and also a first gas introducing valve 40 is connected thereto.

A discharge portion of a humidifying bottle 48 is connected to the first gas introducing valve 40, and an introducing portion of the humidifying bottle 48 branches to be connected to the gas common pipe 47 via a second gas pressure adjusting valve 49. Another branch is connected to a pressure control valve 51 via a filter 50, and to the upstream thereof, a mixed gas cylinder 52 containing $CO_2$ and $O_2$ is connected. The gas cylinder 52 is a cylinder containing $CO_2$ gas filling it while being pressurized at a gas concentration optimized for cell culture, is aimed for pH value adjustment of a liquid medium in the cell culture, and allows gas replacement through a surface of the liquid medium with $CO_2$ gas. The humidifying bottle 48 contains sterile water, and feeds $CO_2$ gas humidified by being caused to pass through the sterile water to a culture container; thereby, it is possible to prevent condensation of liquid medium components due to evaporation of the liquid medium. Thereby, $CO_2$ gas derived from the cylinder 52 is humidified to an optimal humidity and is kept waiting in the humidifying bottle 48.

At the liquid feed pump 41, a first connection 53 and a second connection 54 are provided. In addition, the first connection 53 and second connection 54 are connected to a second gas introducing valve 55. The second gas introducing valve 55 plays a role of a bypass for the liquid feed pump 41.

The second connection 54 at the liquid feed pump 41 branches at a branch point 56, and is connected to a third gas introducing valve 58 that performs open/close control of a gas feed pipe 57 and a gas feed valve 60 that performs open/close control of a gas feed pipe 59. A cell suspension is contained in a cell bottle 61 which is a second liquid containing unit. The cell bottle 61 is connected to the gas feed pipe 59 via a filter 62 connected to a lid of the cell bottle 61. Another pipe is a supply pipe 63 to function as a second supply pipe, having one end which is an open end inside the cell bottle 61, contacts the cell suspension, and serves as a liquid discharge port. A third control valve 64 performs open/close control of the supply pipe 63. The supply pipe 57 branches off from the supply pipe 63 at a branch point 65, and is, at one end thereof, connected to a fourth control valve 68 that performs open/close control of a supply pipe 67 at a branch point 66.

A replenishment medium used for a replacement medium is contained in the replenishment bottle 69. The replenishment bottle 69 is connected to a gas pressure adjusting pipe 71 via a filter 70 connected to a lid of the replenishment bottle 69, and one end of the supply pipe 67 has an open end inside the replenishment bottle 69, contacts the replenishment medium, and serves as a liquid discharge port. That is, pipes are configured such that the replacement medium in the replenishment bottle 69 is fed to the second medium bottle 43 by an action of the liquid feed pump 41.

The common pipe 42 is connected to the gas pressure adjusting pipe 71 of the replenishment bottle 69 and a gas pressure adjusting pipe 72 at the second medium bottle 43 via a third gas pressure adjusting valve 77 and the first gas pressure adjusting valve 76. Furthermore, the common pipe 42 is connected to a gas bag 74 via a filter 73 and is connected to the abovementioned second gas pressure adjusting valve 49. This gas bag 74 is provided with a check valve 75 and communicates with a gas phase in the incubator 32. A gas in the gas cylinder 52 can be contained in the gas bag 74 by opening only the second gas pressure adjusting valve 49. Furthermore, because a volume of gas having exceeded the capacity of the gas bag 74 is released to the gas phase in the incubator 32 due to the check valve 75, the gas pressure in the gas bag 74 is always maintained at atmospheric pressure. That is, it is configured such that the gas contained in the gas bag 74 contacts a gas phase in the replacement medium bottle 43 and a gas phase in the replenishment bottle 69 via the common pipe 42. Furthermore, it is configured such that if the gas pressure adjusting valve 76, first control valve 38 and second control valve 45 are opened, it contacts a liquid phase in the second medium bottle 43 and a liquid phase in the seeding medium bottle 34.

The supply pipe 57 is connected to a multibranched portion 78 that leads to a culture container, and is connected to a container open/close valve 82 for liquid feed in the first culture container 80 and a container open/close valve 83 for a second culture container 81. Because both the first culture container 80 and the second culture container 81 have the same configuration, the first culture container 80 is representatively explained below about its configuration.

The first culture container 80 is an airtight container having an external appearance that includes a body portion 84 and a lid portion 85, and has an internal appearance that can contain a container 87 capable of containing and culturing a cell suspension 86 at the inner bottom portion of the body portion 84. The lid portion 85 is provided with three penetrating ports. One of them is a liquid feed port 88 for adding a liquid to the container 87 and is connected to the abovementioned container open/close valve 82. Another one of them is a discharge port 89 which contacts portions near the bottom surface of the container 87 and is for discharging a liquid, and the last one of them is a gas pressure adjusting port 90. Among them, the liquid feed port 88 doubles as a gas feed port at the time of gas introduction, and because of this, open ends of the liquid feed port 88 and gas pressure adjusting port 90 are provided at the height at which they do not contact the liquid even if the container 87 is filled with the liquid. The gas pressure adjusting port 90 is connected to a fourth gas pressure adjusting valve 91, and is connected to a trap bottle 93 through a multibranched portion 92 at which it branches off to the second culture container 81. The trap bottle 93 is installed in the refrigerator 33, and a gas phase that passes the trap bottle 93 is released to the refrigerator 33 via a filter 94.

A configuration of discharging, from the first culture container 80 or second culture container 81, a liquid contained therein is explained. A liquid discharge pipe 98 is connected to a liquid discharge bottle 97 airtightly. The liquid discharge pipe 98 is connected to the exhaust port of a liquid discharge pump 96 via a discharge valve 99. To the suction port of the liquid discharge pump 96, a first container discharge valve 101 for the first culture container 80 and a first container discharge valve 102 for the second culture container 81 that branch off at a multibranched portion 100 are connected. The first container discharge valve 101 is connected to the discharge port 89 at the first culture container 80. That is, the liquid discharge bottle 97 has a configuration of pipes in which due to an action of the liquid discharge pump 96, a liquid is discharged from the container 87 at the first culture container 80 or the second culture container 81. The various solenoid valves, pump 96, thermostat 32, refrigerator 33 or the like shown above are controlled by a controller 103 which is a control unit.

<Manipulation of Cell Culture>

Figure 6:
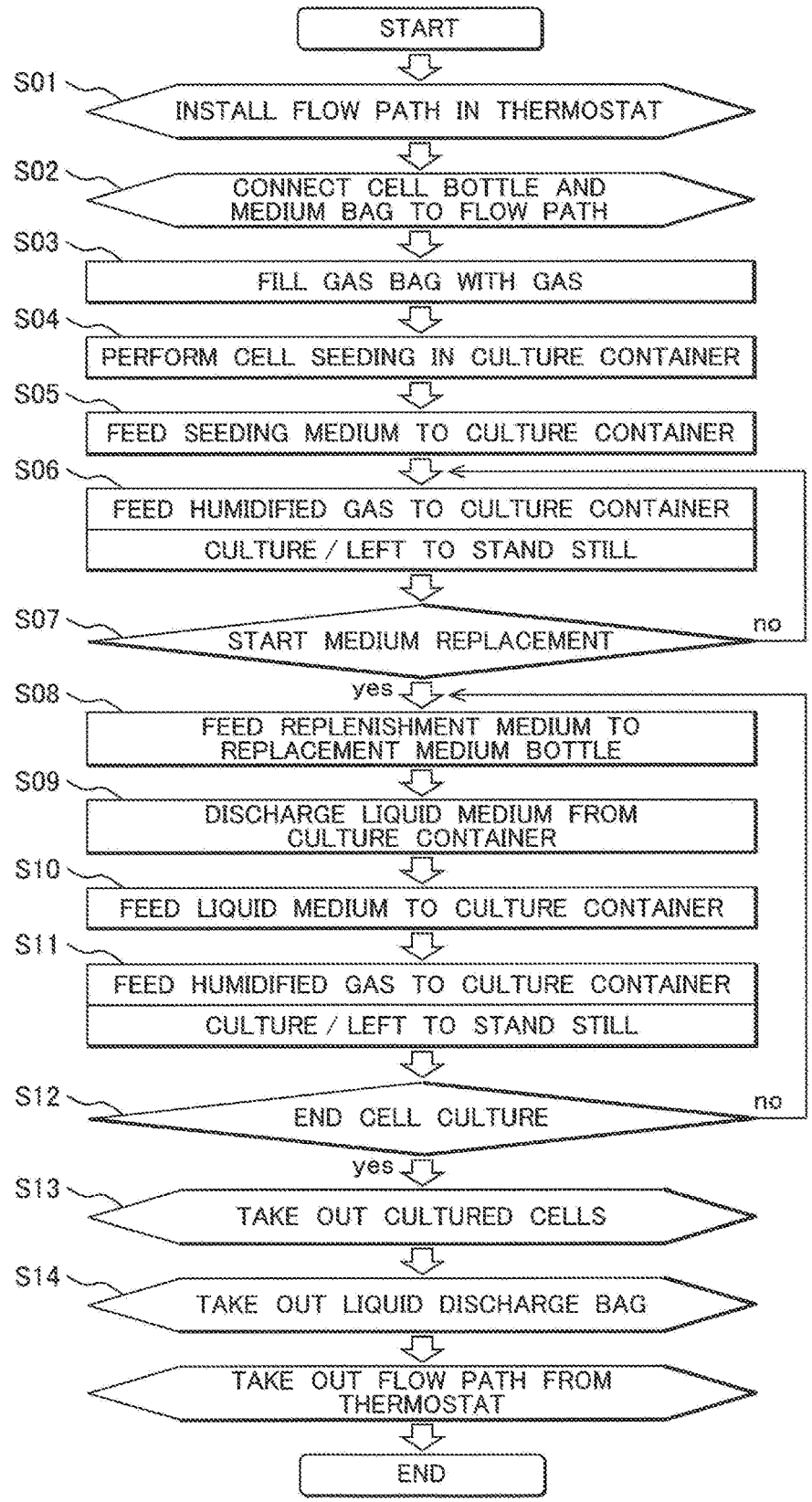
FIG. 6 is a figure showing one example of a control flow of an automatic culture device in Example 1.

FIG. 6 is a figure showing a flowchart of overall manipulation of cell culture in the cell culture device 31 controlled by the controller 103 which is a control unit shown in FIG. 5. Following "START", a flow path is installed in the thermostat 32 (S01), and then the cell bottle 61 containing a separately prepared cell suspension, the medium bottle 34 containing a seeding medium and the replacement medium bottle 69 containing a replacement medium are connected to the flow path (S02). Next, the gas bag 74 is filled with a gas by automatic control (S03). After feeding a gas to the first culture container 80 and second culture container 81, the cell suspension is fed from the cell bottle 61 (S04). Immediately, a seeding medium is fed from the seeding medium bottle 34 to the culture containers (S05). After stirring the cell suspensions in the respective culture containers by an oscillating mechanism not illustrated, a humidified gas is fed to the culture containers, and cells are left to stand still while being kept at a constant temperature (S06). According to the state of progress of the cell culture, it is judged whether to start replacement of the liquid medium (S07). In replacement of the liquid medium, after the second medium bottle 43 is filled with a predetermined volume from the replenishment medium bottle 69 (S08), an old medium in the culture containers is discharged (S09), and then a new liquid medium is fed from the second medium bottle 43 (S10). Subsequently, a humidified gas is fed, and the cells are left to stand still (S11), it is judged whether to continue culture according to the state of progress of the cell culture (S12), and when necessary, replacement of the medium is executed again. At the time of ending the cell culture, the automatic culture is ended, cultured cells are taken out of the culture containers manually (S13), the liquid discharge bag 97 is collected to check whether cells have grown (S14), the used flow path is detached from the thermostat 32 and the process ends (END).

Figure 7:
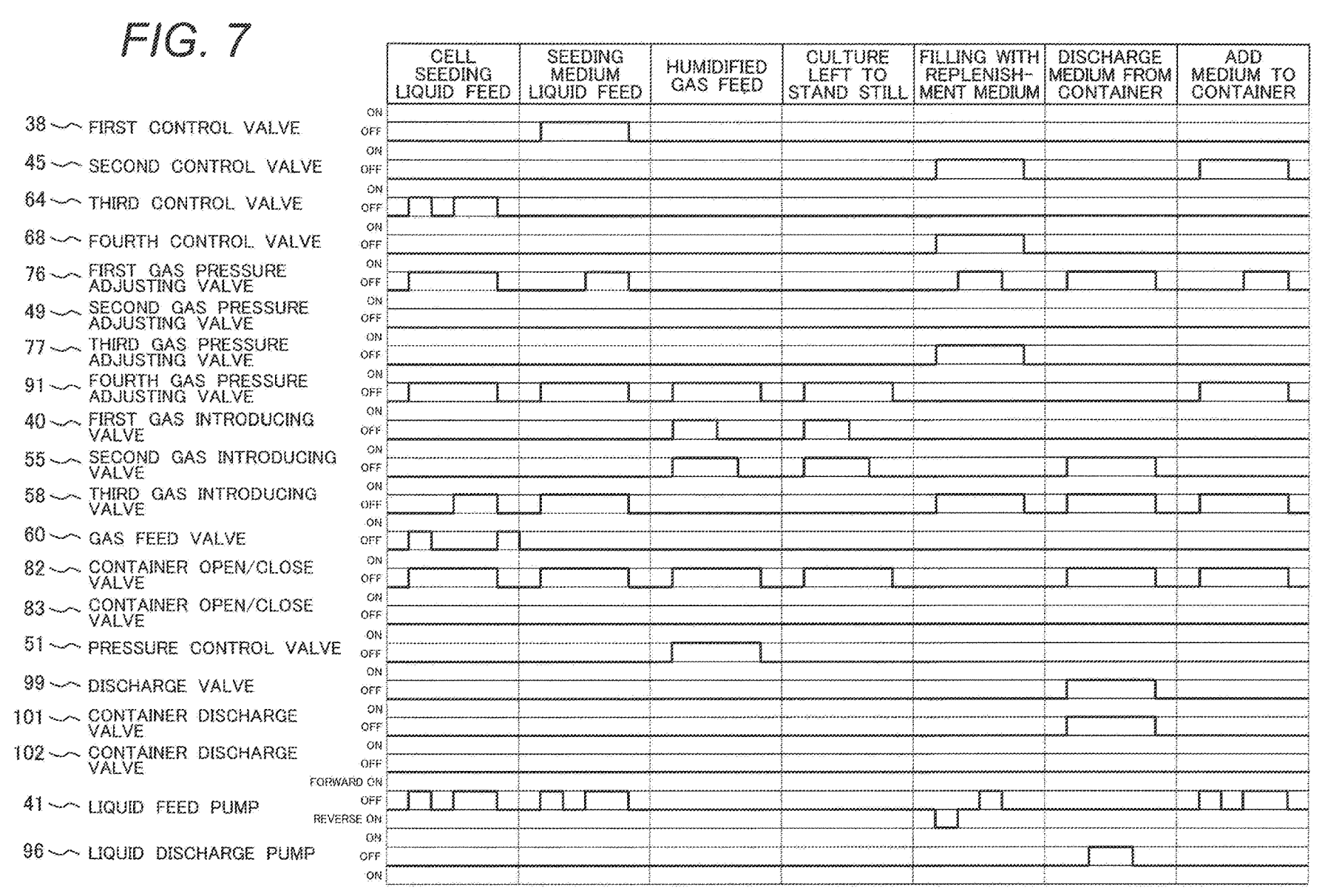

FIG. 7 shows one example of a time chart of liquid feed/gas feed in the culture container 80, which is controlled by the controller 103 in FIG. 5. The horizontal axis indicates manipulation items and the time axis. In the vertical direction, operation timing of 18 solenoid valves, the first control valve 38 to container discharge valve 102 clearly shown in FIG. 5, and roller pumps, the liquid feed pump 48 and liquid discharge pump 96, and the like is shown. In the initial state, all the solenoid valves are turned off, and accordingly are closed, and all the pump are turned off. So liquid feed is stopped.

When cell seeding is performed in the container 87 in the cell culture container 80 (S04 in FIG. 6), operation following the procedure of cell seeding is performed. If, starting from the initial state, the first gas pressure adjusting valve 76, gas feed valve 60 and third control valve 64 are opened, and furthermore the container open/close valve 82 and fourth gas pressure adjusting valve 91 are turned on (opened), the gas bag 74 becomes further communicating with the cell bottle 61 and culture container 80 through the liquid feed pump 41, and furthermore the trap bottle 93 becomes communicating therewith. Next, if the liquid feed pump 41 is kept turned on for a predetermined length of time, liquid feed of the cell suspension from the cell bottle 61 is started, and the liquid feed start point arrives at the container 80. When the volume of liquid that has arrived at the branch point 65 reached a target volume, liquid feed of the liquid feed pump 41 is stopped.

Next, if the third control valve 64 is closed, the gas feed valve 60 is closed, and next the third gas introducing valve 58 is opened to start liquid feed of the liquid feed pump 41, a cell fluid suspension is fed from the first port 88 of the culture container 80 through the container open/close valve 82. At this time, the third port 90 communicates with external air through the trap bottle 93, so the pressure inside the cell culture container 80 is adjusted to be the normal pressure. When the rear end of the cell suspension arrives at the culture container 80, injection of a predetermined volume of the cell suspension is completed, and the liquid feed pump 41 is stopped.

Next, after the internal pressure of the cell bottle 61 is released by opening and closing the gas feed valve 60, respective opened valves are turned off and closed to end the liquid feed. Although not illustrated in the time chart, an effective method of bringing the internal pressure of the cell bottle 61 to the normal pressure may also be a method in which when the volume of a liquid that has arrived at the branch point 65 reached a target volume, and liquid feed of the liquid feed pump 41 is stopped, the third control valve 64 is closed and the second gas introducing valve 55 is opened, thereby introducing a gas in the gas bag.

When there is a plurality of receptacles like the cell culture containers 80, 81, a volume of a cell suspension that is large enough to be able to be distributed to the plurality of cell culture containers is preliminarily contained in the cell bottle 61. If in the abovementioned manipulation, the container open/close valve 82 is closed, the container open/close valve 83 in FIG. 5 is opened, the fourth gas pressure adjusting valve 91 is opened as appropriate, and the abovementioned operation is performed, the same volume of a cell fluid suspension can be fed to the cell culture container 81.

When liquid feed of a seeding medium to the container 87 in the cell culture container 80 is performed (S05 in FIG. 6), operation following the procedure of seeding medium liquid feed is performed. If, starting from the initial state, the first control valve 38 and third gas introducing valve 58 are opened, and furthermore the container open/close valve 82 and fourth gas pressure adjusting valve 91 are turned on (opened), the seeding medium bottle 34 becomes communicating with the culture container 80 through the liquid feed pump 41, and furthermore the trap bottle 93 becomes communicating therewith. Next, if the liquid feed pump 41 is kept turned on for a predetermined length of time, liquid feed of a seeding medium from the seeding medium bottle 34 is started, and the liquid feed start point arrives at the container 80.

When the volume of liquid that has arrived at the branch point 39 reached a target volume, liquid feed of the liquid feed pump 41 is stopped. Next, if the first gas pressure adjusting valve 76 and first control valve are opened, the seeding medium in the supply pipe 37 is divided at the branch point 39, and liquid on the seeding medium bottle 34 side returns to the bottle due to a difference in elevation.

Next, if liquid feed of the liquid feed pump 41 is started, a seeding medium is fed from the first port 88 of the culture container 80 through the container open/close valve 82. At this time, the third port 90 communicates with external air through the trap bottle 93, so the pressure inside the cell culture container 80 is adjusted to be the normal pressure. When the rear end of the seeding medium arrives at the culture container 80, injection of a predetermined volume of the seeding medium is completed, the liquid feed pump 41 is stopped, and respective opened valves are turned off and closed to end the liquid feed.

When there is a plurality of cell culture containers, a volume of a seeding medium that is large enough to be able to be distributed to the plurality of cell culture containers is preliminarily contained in the seeding medium bottle 34. If in the abovementioned manipulation, the container open/close valve 82 is closed, the container open/close valve 83 in FIG. 5 is opened, the fourth gas pressure adjusting valve 91 is opened as appropriate, and the abovementioned operation is performed, the same volume of a seeding medium can be fed to the cell culture container 81.

Next, when the inside of the culture container 80 is filled with a humidified $CO_2$ gas (S06 in FIG. 6), operation following the manipulation of humidified gas feed to the culture container is performed. If, starting from the initial state, the first gas introducing valve 40 and second gas introducing valve 55 are opened, and furthermore the container open/close valve 82 and fourth gas pressure adjusting valve 91 are turned on (opened), the humidifying bottle 48 becomes communicating with the culture container 80, and furthermore the trap bottle 93 becomes communicating therewith. Next, if the pressure control valve 51 is opened while being adjusted to a predetermined pressure, and the first gas introducing valve 40 is turned on for a predetermined length of time, an optimally humidified $CO_2$ gas arrives at the culture container 81 from the cylinder 52 through the humidifying bottle 48. Because although the culture container 81 is tightly closed, the third port 90 to the filter 94 communicating with external air are opened, the pressure inside the culture container becomes a pressure adjusted to the pressure of the external air. After a predetermined volume of the $CO_2$ gas is injected, first, the first gas introducing valve 40 is closed, next, the second gas introducing valve 55 is closed, and when the pressure in the culture container became comparable to the atmospheric pressure, the container open/close valve 82 and fourth gas pressure adjusting valve 91 are closed.

When there is a plurality of cell culture containers, if in the abovementioned manipulation, the container open/close valve 83 and fourth gas pressure adjusting valve 91 are opened, and the abovementioned operation is performed, the culture container 81 is filled with $CO_2$ gas.

Next, if it is determined to perform replacement of a liquid medium from a cell culture container (S07 in FIG. 6), operation following the manipulation of filling of the replenishment medium (S08 in FIG. 6) in the operation time chart of FIG. 7 is performed.

Starting from the initial state, the third gas pressure adjusting valve 77, second control valve 45, third gas introducing valve 58 and fourth control valve 68 are opened. As a result, the second medium bottle 43 becomes communicating with the replenishment medium bottle 69 via the liquid feed pump 41. Next, a liquid is fed from the liquid feed pump 41 in the direction opposite to the normal direction. When the front end of the liquid arrives at the second medium bottle 43 and the volume of liquid that has reached a target volume, liquid feed of the pump 41 is stopped. Next, if the first gas pressure adjusting valve 76 is opened, the liquid is divided at the branch point 46 in the supply pipe 44, and a liquid in the supply pipe 44 on the second medium bottle 43 side which is the current liquid feed direction is fed to the second medium bottle 43 due to a difference in elevation. That is, the target liquid volume is the volume of a liquid having been fed to the second medium bottle 43 and the volume of a liquid contained in the branch point 46 in the supply pipe 44.

Next, if a liquid is fed from the liquid feed pump 41 in the normal liquid feed direction, a liquid having a rear end at the position of the branch point 66 starts being moved, and the liquid arrives at the replenishment medium bottle 69 where it was originally. At this time, because the gas phase of the second medium bottle 43 is communicating with the gas phase of the replenishment medium bottle 69 through the gas pressure adjusting pipe 71, the pressures inside the second medium bottle 43 and the replenishment medium bottle 69 are adjusted to the normal pressure. Respective opened valves are turned off and closed to end the liquid feed.

When there is a plurality of cell culture containers, the feeding volume of a pump is adjusted such that a volume of a liquid medium that is large enough to be distributed to the plurality of cell culture containers is preliminarily contained in the second medium bottle 43. In addition, if it is planned in cell culture to replace a medium multiple times, by making, contained in the replenishment medium bottle 69, the volume of liquid medium that enables feeding of the liquid medium that is obtained by multiplying the liquid medium volume necessary when there is a plurality of cell culture containers by the number of times of replacement of the medium, consecutive replacement of the medium multiple times for the plurality of cell culture containers is possible.

When a medium is discharged from the container 87 in the culture container 80 (S09 in FIG. 6), operation following the operation of discharging a medium from a container in the operation time chart of FIG. 7 is performed. If, starting from the initial state, the first gas pressure adjusting valve 76, second gas introducing valve 55, third gas introducing valve 58 and container open/close valve 82 are opened and the container discharge valve 101 and discharge valve 99 are turned on (opened), a communicating pipeline is created from the gas bag 74 through the first gas pressure adjusting valve 76 to the first port 88 of the second culture container 81. In addition, a communicating flow path is created from the liquid discharge bottle 97 via the discharge pump 96 to the discharge port 89. Next, after discharge time for the discharge pump 96 to discharge a volume of liquid contained in the container 87 is given and the discharge pump 96 is turned on for a predetermined length of time, liquid feed is started by suctioning a liquid medium from the container, and the liquid medium arrives at the liquid discharge bottle 97. At this time, because the first port 88 is communicating with the gas bag, the pressure inside the cell culture container 55 is adjusted to the normal pressure, and the gas in the gas bag is introduced thereto. After a predetermined volume of the liquid is discharged, the discharge pump 96 is stopped, respective opened valves are turned off and closed to end the liquid feed.

When there is a plurality of cell culture containers, in the abovementioned manipulation, the container open/close valve 82 is closed, the container open/close valve 83 in FIG. 5 is opened, the container discharge valve 101 is closed, the container discharge valve 102 is opened, and the abovementioned operation is performed, a liquid medium can be discharged from the container in the culture container 81.

When addition of a liquid medium to the container 87 in the culture container 80 is performed (S10 in FIG. 6), operation following the procedure of addition of a medium to a container is performed. If the second control valve 45 and third gas introducing valve 58 are turned on (opened), and furthermore the container open/close valve 82 and fourth gas pressure adjusting valve 91 are turned on (opened), the second medium bottle 43 becomes communicating with the culture container 80 through the liquid feed pump 41, and furthermore the trap bottle 93 becomes communicating therewith. Next, if the liquid feed pump 41 is kept turned on for a predetermined length of time, liquid feed of a replacement medium from the second medium bottle 43 is started, and the liquid feed start point arrives at the container 80.

When the volume of liquid that has arrived at the branch point 39 reached a target volume, liquid feed of the liquid feed pump 41 is stopped. Next, if the first gas pressure adjusting valve 76 is opened, the replacement medium in the supply pipe 44 is divided at the branch point 46, and liquid on the second medium bottle 43 side returns to the bottle due to a difference in elevation. Next, if liquid feed of the liquid feed pump 41 is started, a replacement medium is fed from the first port 88 of the culture container 80 through the container open/close valve 82. At this time, the third port 90 communicates with external air through the trap bottle 93, so the pressure inside the cell culture container 80 is adjusted to be the normal pressure. When the rear end of the replacement medium arrives at the culture container 80, injection of a predetermined volume of the replacement medium is completed, the liquid feed pump 41 is stopped, and respective opened valves are turned off and closed to end the liquid feed.

When there is a plurality of cell culture containers, a volume of a liquid medium that is large enough to be able to be distributed to the plurality of cell culture containers is preliminarily contained in the second medium bottle 43. If in the abovementioned manipulation, the container open/close valve 82 is closed, the container open/close valve 83 in FIG. 5 is opened, the fourth gas pressure adjusting valve 91 is opened as appropriate, and the abovementioned operation is performed, the same volume of a replacement medium can be fed to the cell culture container 81.

Subsequently, when the inside of the culture container 80 is filled with a humidified $CO_2$ gas (S11 in FIG. 6), operation following the section about humidified gas feed explained above may be performed.

As explained above, in the example of the cell culture device shown in FIG. 5, it can be said that automatic cell culture is possible by management conforming to the operation sequence shown in FIG. 6 and the detailed time chart shown in FIG. 7 in the following manner: the culture container 80 is kept at an optimal culture temperature by the incubator 32; a cell suspension can be fed to a culture container by a liquid feed device; then, due to a gas feed mechanism, a liquid medium is maintained in a suitable $CO_2$ gas environment and under a suitable humidity condition; because cells grow adhering to the inner bottom surface of the container 87, a liquid medium having been subjected to composition change along with culture can be suctionally discharged, and the cells and the liquid medium can be separated thereby; the second medium bottle 43 contained in the thermostat 32 in a suitable volume can be filled with a replacement medium and it can be contained therein while being preheated; next, a replacement medium is sequentially added to a culture container and medium replacement can be performed thereby.

According to the liquid feed device of the present example, a liquid that is desired to avoid as much as possible influence of pressure changes in the liquid to be the source of liquid feed is contained in the second liquid bottle, and a liquid that is less susceptible to influence of pressure changes in the liquid to be the source of liquid feed is contained in the first liquid bottle; thereby, the liquid that is desired to avoid as much as possible influence of pressure changes can be fed to a target container with reduced influence of passing though the pump; on the other hand, the liquid that is not susceptible to influence of pressure changes can pass the pump, and be fed to a target container quantitatively repetitively.

As explained above, according to the liquid feed device and cell culture device described in Example 1, it can be said that a first problem that cells or a biological sample are/is damaged by pressure changes accompanying liquid feed can be solved, and furthermore automatic cell culture is possible. A reason for this is because the liquid that is desired to avoid as much as possible influence of pressure changes is contained in the second liquid bottle arranged downstream of the pump and is fed to the target container by pressure propagation via a gas phase; thereby, it can be fed to the target container. In addition, on the other hand, another reason for that is because the liquid that is not susceptible to influence of pressure changes is contained in the first liquid bottle arranged upstream of the pump, and fed by passing the pump; as a result, it can be fed to the target container repetitively by quantitative control according to the flow rate accuracy of the pump. At this time, if a cell suspension is contained in the second liquid bottle, the concern about damages to cells or a biological sample due to pressure changes accompanying liquid feed can be mitigated. If a liquid medium or the like is contained in the second liquid bottle, the liquid medium can be fed quantitatively repetitively.

Furthermore, the liquid feed device of the present example and the cell culture device using the same provide the following effects. In the flowchart shown in FIG. 6, a cell suspension is fed first, and next a seeding medium is fed later. At this time, after the cell suspension is fed first, there might be the cell suspension remaining as a small number of droplets in the liquid supply pipe communicating through to the culture container. Because when the seeding medium or the like is fed thereafter, it passes through the liquid supply pipe, it can mix with the small number of droplets containing the cell suspension to arrive at a target container. Due to an effect of so-called prewashing, there is an effect of being able to reduce influence of cells remaining in the pipe.

Example 2

In Example 2, in addition to having the configuration of the liquid feed device explained in Example 1, the liquid feed device can check a liquid feed volume by the following method. That is, in addition to having the configuration of Example 1, the liquid feed device of the present example includes weight sensors that respectively detect weights of a first liquid in a first liquid containing unit and a second liquid of a second liquid containing unit, and the control unit is configured to control the pump according to outputs of the weight sensors.

Figure 8:
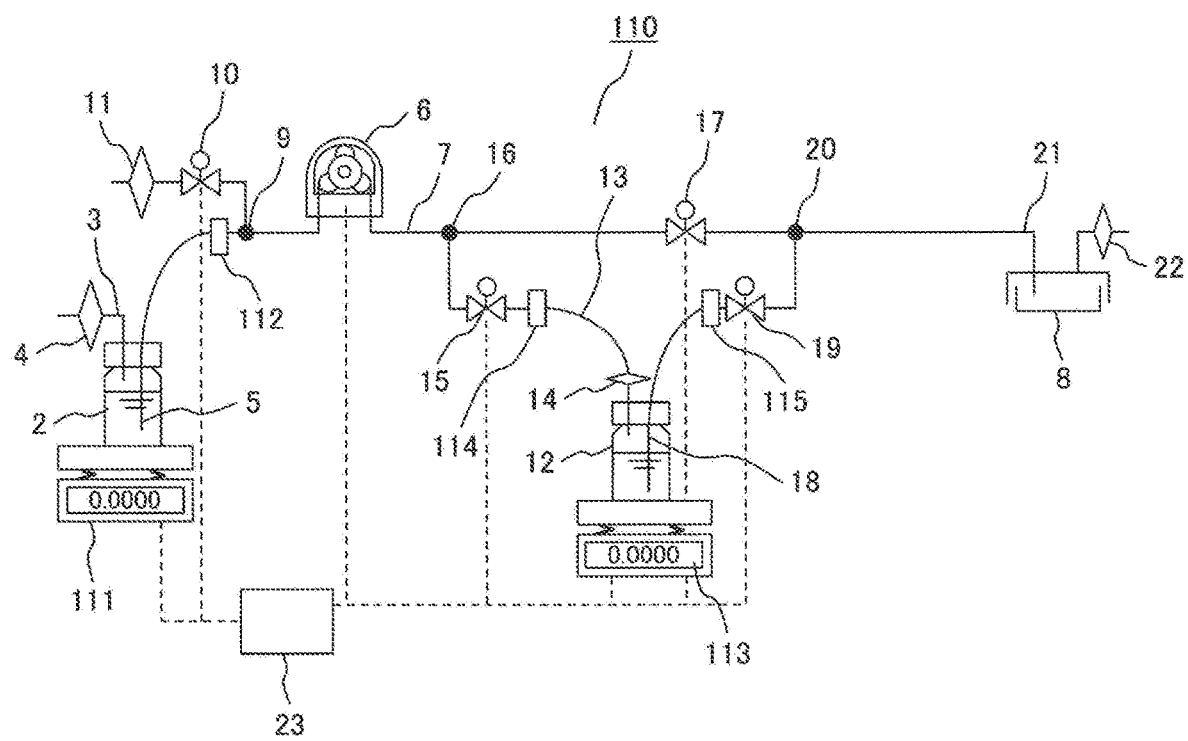
FIG. 8 is a figure of one configuration of a liquid feed device in Example 2.

FIG. 8 is a figure showing the configuration of a liquid feed device 110 in Example 2. Although it has a basic configuration which is the same as that in Example 1, a configuration of sensing values about weight changes of the liquid bottles is added to be capable of a method of checking liquid feed volumes. That is, it has a configuration which is the same as that Example 1 shown in FIG. 1 having the first liquid bottle 2, gas pressure adjusting pipeline 3, filter 4, supply pipe 5, pump 6, supply pipe 7, receptacle 8, branch point 9, first gas introducing valve 10, filter 11, second liquid bottle 12, gas pipeline 13, filter 14, second gas introducing valve 15, branch point 16, first supply valve 17, supply pipe 18, second supply valve 19, branch point 20, liquid supply pipe 21, filter 22 and the controller 23 constituting the control unit.

In the present example also, the branch point 9 is provided above the liquid surface of the liquid in the first liquid bottle contained in the first liquid bottle 2 of the supply pipe 5. Thereby, it is possible to cause a liquid in the supply pipe 5 between the position of the branch point 9 and the first liquid bottle 2 to return to the liquid bottle 2 by means of the potential energy generated due to a difference in elevation of the liquid when the first gas introducing valve 10 is opened and a gas is fed, and clogging can be prevented. Furthermore, when the weight of a liquid bottle before and after liquid feed explained below is measured, it is desirable to cause the liquid to return to the liquid bottle 2, and the volume of the liquid remaining in the pipe is 0.

The configuration of the present example includes: a first weight sensor 111 that measures a weight of a set of the first liquid bottle 2 containing a liquid, the gas pressure adjusting pipeline 3 and the filter 4; and a fixing jig 112 that fixes the supply pipe 5. A pipe material such as a highly flexible rubber tube is preferably used for the supply pipe 5 because constituent parts connected downstream of the branch point 9 do not impair weight measurement of the first liquid bottle 2. Furthermore, the configuration of the present example includes: a second weight sensor 113 that measures a weight of a set of the second liquid bottle 12 containing a liquid, the gas pipeline 13, the filter 14 and the supply pipe 18; a fixing jig 114 that fixes the gas pipeline 13; and a fixing jig 115 that fixes the supply pipe 18. The fixing jigs 114, 115 are both added for a purpose similar to that for the fixing jig 112.

Figure 9:
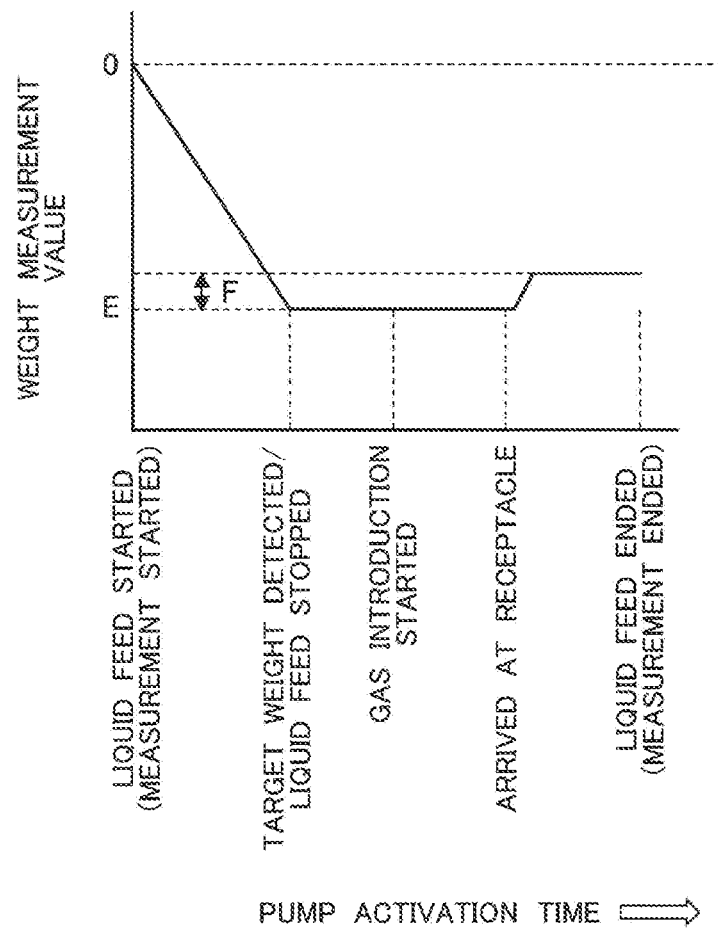
FIG. 9 is a figure showing control of the liquid feed device in Example 2 and a weight measurement data example.

The liquid feed device 110 of the present example feeds liquid and checks a liquid feed volume in the following manner. In FIG. 9, the order of control in the present example is shown along the horizontal axis, and the vertical axis shows weight measurement values obtained by the weight sensors corresponding to it. As an example of weight measurement, the liquid feed method performed for a liquid in the second liquid bottle 12 and changes in measurement values of the weight sensor 113 are explained. The weight measurement value of the second weight sensor 113 before liquid feed is measured, and this is assumed to be zero here. If the first supply valve 17 is closed, the first gas introducing valve 10, second gas introducing valve 15 and second supply valve 19 are opened, and then the pump 6 is activated, a gas is introduced through the filter 11, and additionally the pump 6 starts pressurization through the branch point 9 on a liquid in the second liquid bottle 12. The liquid in the second liquid bottle 12 passes the second supply valve 19 through the supply pipe 18, liquid feed to the container 8 is started thereby, and along with it, the weight decreases.

Simultaneous with the target value weight E being reached, the pump 6 is stopped, the second supply valve 19 is closed, and next the second gas introducing valve 15 is closed. The supply pipe 18 is blocked, and a liquid does not move therethrough. Next, if the first supply valve 17 is opened and the pump 6 is activated, a gas is introduced through the filter 11, and the gas moves through the branch point 16 and first supply valve 17, a liquid downstream of the position of the branch point 20 on the container side starts moving and the volume of this liquid on the container 8 side is the object liquid feed volume. The front end of the liquid arrives at the receptacle 8, addition of the liquid is started thereby, and if the rear end of the liquid arrives at the receptacle 8, the pump 6 is stopped. Next, if the second gas introducing valve 15 and second supply valve 19 are opened, the liquid in the supply pipe 18 returns into the second liquid bottle 12 due to a difference in elevation, and the weight measurement value of the weight sensor 113 at that time is measured and liquid feed is ended.

The target value weight E is a weight obtained by adding, to the weight-converted value of a liquid feed volume of a target liquid which is obtained based on its liquid volume and density, a weight F of a liquid filling the volume of the supply pipe 18 having a length from the branch point 20 to the liquid surface of a liquid in the liquid bottle 2, the weight F being obtained based also on the density of the liquid. That is, a liquid feed volume of a liquid fed to the container 8 can be detected based on a weight measurement value obtained according to E-F. When a liquid is fed repetitively, a successively decreasing weight can be handled as a fed liquid weight by executing the abovementioned manipulation.

The liquid feed device of the present example can be used for checking a fed volume of a cell suspension at the time of cell seeding. Generally, at the step of cell culture, execution of such dispensing steps is guaranteed by proficiency of workers and work implementation records. By using the present example, it is possible to guarantee sure execution results of cell culture steps by recording that change amounts of the weight of a cell bottle to be the source of liquid feed has reduced by a target weight and handling such a record as a work record of single event of dispensing. In addition, although if a pump is used for a long time, the shape deformation and restoration capability of a tube gets deteriorated, and the pump flow rate changes in some cases, even if such a change occurs, the liquid feed method controls liquid feed based on change amounts of the weight of a liquid to be fed as a result, and is thus can be said to provide good reproducibility. Additionally, if operation information obtained from the automatic device such as records of time during which all the pumps are actuated, records about voltages applied to the pumps or actuation time records of liquid surface sensors is organized, execution results of liquid feed and discharge can be guaranteed highly reliably.

Furthermore, by applying the liquid feed device of the present example to the cell culture device shown in Example 1, the load applied onto cells, a biological sample or the like due to pressure changes accompanying liquid feed can be reduced, furthermore liquid feed can be performed while at the time the liquid feed volume is controlled accurately, and furthermore automatic cell culture can be enabled.

Example 3

In Example 3, in addition to having the configuration of the liquid feed device explained in Example 1, the liquid feed device can feed a very small liquid feed volume with good reproducibility by the following method. That is, this is an example of: a liquid feed device including a first liquid bottle containing a first liquid, a supply pipe through which the first liquid passes, a gas introducing valve, the gas introducing valve, the liquid bottle, a second liquid bottle containing a liquid that is desired to avoid as much possible influence of pressure changes, a supply pipe through which a second liquid passes, a pump and a target container, the liquid feed device being characterized by connecting the container at the downstream of the second liquid bottle, operating the pump to suction toward itself, and then feeding a liquid to target container; and furthermore a cell culture device including this liquid feed device.

FIG. 10 is a figure showing one configuration of a liquid feed device 120 in Example 3, and shows a configuration a liquid that is desired to avoid as much as possible influence of pressure changes in a liquid to be the source of liquid feed is retained in a supply pipe in a required volume, and then the liquid is fed to a target container repetitively quantitatively. That is, it has the same configuration as that Example 1 in that it includes the first liquid bottle 2, gas pressure adjusting pipeline 3, filter 4, supply pipe 5, pump 6, supply pipe 7, receptacle 8, branch point 9, first gas introducing valve 10, filter 11, second liquid bottle 12, filter 14, supply pipe 18, second supply valve 19, branch point 20, liquid supply pipe 21, filter 22 and controller 23. Furthermore, 121 includes a retention pipe 121 joined with the supply pipe 7 and the supply pipe 18 at the branch point 20, and furthermore a first supply valve 122 that controls the liquid supply pipe 21 connected to the retention pipe 121. The retention pipe 121 has a known length and pipe diameter, and may have the same diameter as that of other pipes which are the supply pipe 7, supply pipe 18 and liquid supply pipe 21. Here, it is expressed differently for explanation.

The liquid feed device 120 of the present example feeds liquid and checks liquid feed volume as shown next. FIG. 11 shows one example of a control flowchart of the present example. At the time of second liquid addition, that is, at the time of feeding of a second liquid, the first gas introducing valve 10, and second supply valve 19 are opened, then the pump 6 is activated in the suction direction opposite to the target liquid feed direction, and liquid feed of the second liquid is started thereby. Upon completion of supply of the predetermined liquid volume C from the second liquid bottle 12 through the supply pipe 18 to the retention pipe 121, activation of the pump 6 is promptly stopped.

Next, after the second supply valve 19 is closed, the first supply valve 122 is opened. A length of time which is longer than that required for the rear end of the liquid to arrive at the receptacle 8 is set as the length of time during which the pump 6 is activated, and the pump 6 is operated for the length of time. After the given length of time, the pump 6 is stopped, and then all the valves are closed. At the time of first liquid addition, that is, at the time of feeding of a first liquid, the first supply valve 122 is opened, then the pump 6 is activated in the target liquid feed direction, and the liquid feed of the first liquid contained in the first bottle 2 is started thereby.

With the liquid feed device of the present example, changes in the pressure applied to a cell suspension at the time of cell seeding can be made small, and furthermore the device configuration can also be simplified. As compared with the liquid feed device 1 in Example 1, a retention pipe is used and a liquid such as a cell suspension that is desired to avoid as much as possible influence of pressure changes and a liquid such as a liquid medium which is free of the influence of pressure changes share a supply pipe; thereby, an effect of being able to reduce control valves for controlling the supply pipe is provided.

Figure 12:
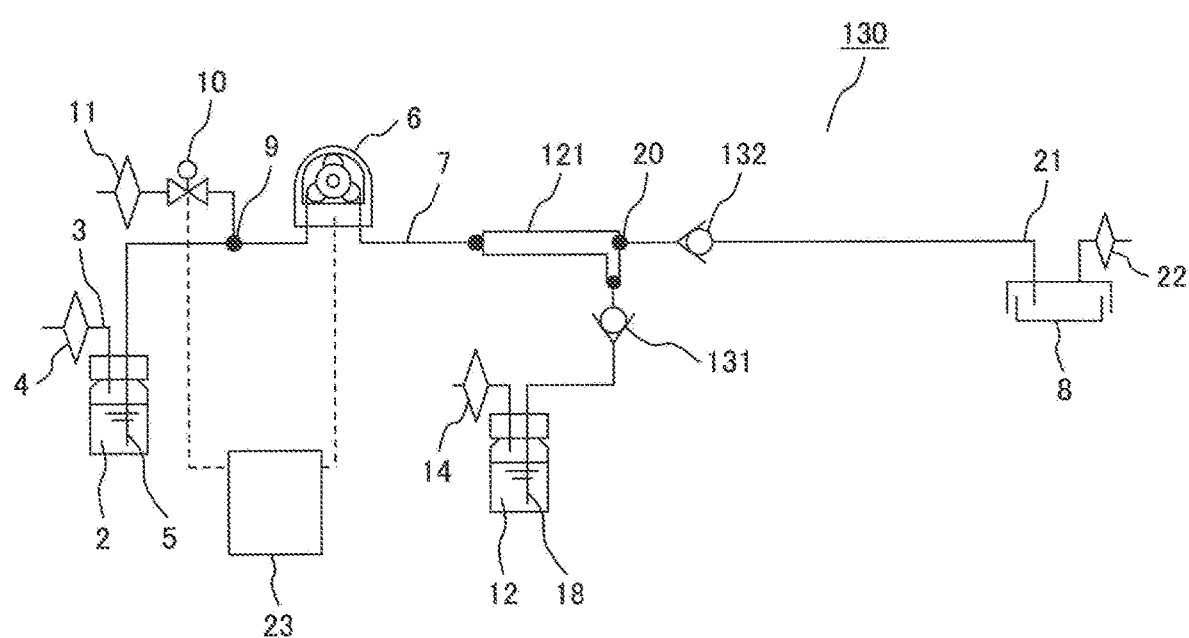
FIG. 12 is a figure of another configuration of the liquid feed device in Example 3.

The liquid feed device in the present example further can solve a problem while simplifying mechanism control. FIG. 12 is a figure showing a variant configuration example in which the basic configuration is the same as the liquid feed device 120 shown in FIG. 10, but check valves 131, 132 are provided along the illustrated direction in place of the second supply valve 19 and first supply valve 122. In more detail, due to the check valves 131, 132, the direction of liquid feed of the supply pipe 18 is always in the suction direction relative to the liquid feed pump 6, and a flow never occurs in the pressurizing direction. On the other hand, the direction of liquid feed of the liquid supply pipe 21 is always in the pressurizing direction relative to the liquid feed pump 6, and a flow never occurs in the suction direction. In this configuration, if the liquid feed pump 6 performs suction operation in the direction opposite to the target receptacle 8, a predetermined volume of the liquid is suctioned from the second bottle, and contained in the retention pipe 121. Then, if the liquid feed pump 6 performs pressurization operation in the direction of the target container 8, the liquid contained in the retention pipe 121 can be fed to the target container 8.

Because there are fewer device configurations to be controlled in this configuration, effects of cost reduction, size-reduction and the like can be attained. In addition, the degree of complication is reduced, and the reliability can be improved. In addition, the retention pipe 121 is changed as appropriate according to the target liquid feed volume, and if the target liquid feed volume is larger, the pipe diameter should be increased to avoid an excessive pipe length. On the other hand, if the target liquid feed volume is very small and accuracy is required, it is also useful to reduce the pipe diameter and reduce the internal surface area of the retention pipe 121.

With the liquid feed device according to the present invention explained above and the cell culture device using the same, a liquid that is desired to avoid as much as possible influence of pressure changes in the liquid to be the source of liquid feed is contained in the second liquid bottle, and a liquid that is less susceptible to influence of pressure changes in the liquid to be the source of liquid feed is contained in the first liquid bottle; thereby, the liquid that is desired to avoid as much as possible influence of pressure changes can be fed to a target container with reduced influence of passing though the pump; on the other hand, the liquid that is not susceptible to influence of pressure changes can pass the pump, and be fed to a target container quantitatively repetitively.

Note that the present invention is not limited to the abovementioned examples, but incorporates various variants. For example, the abovementioned examples are explained in detail for better understanding of the present invention, but are not necessarily limited to those including all the explained configurations. In addition, part of the configuration of an example can be replaced with the configuration of another example, and also the configuration of an example can be added to the configuration of another example. In addition, part of the configuration of each example can be added to, deleted from and replaced by another configuration.

Furthermore, although an example in which a program is created for partially or entirely realizing the abovementioned respective configurations, functions controller which is a control unit is explained, it is needless to say that they may be realized by hardware by designing them partially or entirely for example in an integrated circuit, and so on. That is, all the functions or some of the functions of processing units may be realized for example by an integrated circuit such as an ASIC (Application Specific Integrated Circuit) or an FPGA (Field Programmable Gate Array), instead of being realized by a program.

REFERENCE SIGNS LIST 1, 110, 120, 130: liquid feed device
2: first liquid bottle
3: gas pressure adjusting pipeline
4, 11, 14, 22, 36, 50, 62, 70, 73, 94: filter
5, 7, 18, 37, 44, 57, 63, 67: supply pipe
6: pump
8: receptacle
9, 16, 20, 39, 46, 56, 65, 66: branch point
10: first gas introducing valve
12: second liquid bottle
13: gas pipeline
15: second gas introducing valve
17, 122: first supply valve
19: second supply valve
21: liquid supply pipe
23, 103: controller
31: automatic cell culture device
32: thermostat
33: refrigerator
34: first medium bottle
35, 71, 72: gas pressure adjusting pipe
38: first control valve
42: common pipe
43: second medium bottle
45: second control valve
76: first gas pressure adjusting valve
47: gas common pipe
40: first gas introducing valve
48: humidifying bottle
49: second gas pressure adjusting valve
51: pressure control valve
52: mixed gas cylinder
53: first connection
54: second connection
55: second gas introducing valve
58: third gas introducing valve
59: gas feed pipe
60: gas feed valve
61: cell bottle
64: third control valve
68: fourth control valve
69: replenishment bottle
74: gas bag
75, 131, 132: check valve
78, 92, 100: multibranched portion
80: first culture container
82, 83: container open/close valve
81: second culture container
84: body portion
85: lid portion
86: cell suspension
87: container
88: liquid feed port
89: discharge port
90: gas pressure adjusting port
91: fourth gas pressure adjusting valve
92, 100: multibranched portion
93: trap bottle
96: liquid discharge pump
97: liquid discharge bottle
98: liquid discharge pipe
99: discharge valve
101: first container discharge valve
102: first container discharge valve
111: first weight sensor 112, 114, 115: fixing jig
113: second weight sensor
121: retention pipe

The invention claimed is:

1. A liquid feed device comprising:
a first liquid containing unit that contains a first liquid;
a second liquid containing unit that contains a second liquid;
a pump connected between the first liquid containing unit and the second liquid containing unit;
a receptacle connected downstream of the second liquid containing unit;
a first supply pipe that is configured to supply the first liquid to the receptacle through the pump;
a second supply pipe that is configured to supply the second liquid to the receptacle, with a pressurized liquid feed from the second liquid containing unit; and
a gas introducing valve that is configured to introduce gas into the second liquid containing unit, wherein
the gas introducing valve includes: a first gas introducing valve connected via a first branch point to the first supply pipe, the first supply pipe having a first end thereof that is connected to the first liquid containing unit and having a second end thereof that is connected to the pump, and a second gas introducing valve connected between the pump and the second liquid containing unit,
a first supply valve that is configured to open and close the first supply pipe between the pump and the receptacle,
a second supply valve that is configured to open and close the second supply pipe between the second liquid containing unit and the receptacle; and a control unit that is configured to control the pump, the first supply valve, the second supply valve, the first gas introducing valve and the second gas introducing valve,
the control unit is configured to: i) close the first supply valve, ii) open the first gas introducing valve, the second gas introducing valve, and the second supply valve, and iii) activate the pump, so that the second liquid in the second liquid bottle is passed to the receptacle through the second supply pipe, and
the control unit is configured to: i) close the second gas introducing valve and second supply valve, ii) open the first supply valve, and iii) activate the pump, so that some amount of the second liquid is passed to the receptacle.

2. The liquid feed device according to claim 1,
wherein the control unit is configured to: i) open the first supply valve, ii) operate the pump to feed the first liquid from the first liquid containing unit to the receptacle via the first supply pipe, iii) open the first gas introducing valve, and iv) operate the pump to feed a predetermined volume of the first liquid to the receptacle.

3. The liquid feed device according to claim 1,
wherein the control unit is configured to:
open the second supply valve, the first gas introducing valve, and the second gas introducing valve,
operate the pump to feed the second liquid from the second liquid containing unit to the receptacle via the second supply pipe; and
after closing the second supply valve and the second gas introducing valve, open the first supply valve and operates the pump to feed a predetermined volume of the second liquid to the receptacle.

4. The liquid feed device according to claim 1, further comprising:
a liquid supply pipe that is configured to supply a liquid in the receptacle,
a first supply pipe that is configured to supply the first liquid in the liquid supply pipe via the pump,
a second supply pipe that is configured to supply the second liquid in the liquid supply pipe, and
a second branch point that is configured to branch the first supply pipe and the second supply pipe from the liquid supply pipe, wherein
an opening of the liquid supply pipe is provided above a liquid surface of the second liquid in the second liquid containing unit.

5. The liquid feed device according to claim 3, wherein the control unit is configured to: i) open the second supply valve, the first gas introducing valve, and the second gas introducing valve, ii) cause the pump to perform direct action, and iii) reverse action to stir the second liquid in the second liquid containing unit.

6. The liquid feed device according to claim 1, wherein the first liquid containing unit and the second liquid containing unit are constituted by liquid bottles, respectively, and ratios of diameters of the liquid bottles to diameters of the first supply pipe and the second supply pipe that discharge the first liquid and the second liquid from the liquid bottles are no greater than 1000%.

7. The liquid feed device according to claim 1, wherein the first liquid containing unit and the second liquid containing unit are constituted by liquid bottles, respectively, and bottom surface portions of the liquid bottles have triangular pyramid shapes.

8. The liquid feed device according to claim 1, comprising weight sensors that are configured to detect weights of the first liquid in the first liquid containing unit and the second liquid in the second liquid containing unit, respectively,
wherein the control unit is configured to control the pump according to an output from the weight sensors.

9. A cell culture device comprising:
a thermostat;
a culture container arranged in the thermostat;
a liquid feed device that is configured to feed and discharge a liquid to and from the culture container;
a control unit that is configured to control the thermostat and the liquid feed device,
wherein the liquid feed device has:
a first liquid containing unit that is configured to hold a first liquid;
a second liquid containing unit that is configured to hold a second liquid;
a pump connected between the first liquid containing unit and the second liquid containing unit;
a first supply pipe that is configured to supply the first liquid to the culture container through the pump;
a second supply pipe that is configured to supply the second liquid to the culture container with a pressurized liquid feed from the second liquid containing unit,
a gas introducing valve that is configured to introduce gas into the second liquid containing unit, wherein the gas introducing valve includes: a first gas introducing valve connected via a first branch point to the first supply pipe, the first supply pipe having a first end thereof that is connected to the first liquid containing unit and having a second end thereof that is connected to the pump, and a second gas introducing valve connected between the pump and the second liquid containing unit, and a first supply valve that is configured to open and close the first supply pipe between the pump and the culture container; and a second supply valve that is configured to open and close the second supply pipe between the second liquid containing unit and the culture container, wherein the control unit is configured to: i) open the first supply valve, the first gas introducing valve, the second gas introducing valve, and the second supply valve, ii) activate the pump, so that the second liquid in the second liquid bottle is passed to the culture container through the second supply pipe, iii) close the second gas introducing valve and second supply valve, iv) open the first supply valve, and v) activate the pump, so that some amount of the second liquid is passed to the culture container.

10. The cell culture device according to claim 9, wherein the control unit is also configured to:

open the first supply valve and operate the pump to feed the first liquid from the first liquid containing unit to the culture container via the first supply pipe; and open the first gas introducing valve and operate the pump to feed a predetermined volume of the first liquid to the culture container, open i) the second supply valve, ii) the first gas introducing valve, iii) the second gas introducing valve, operate the pump to feed the second liquid from the second liquid containing unit to the culture container via the second supply pipe; and after closing the second supply valve and the second gas introducing valve, open the first supply valve, and operate the pump to feed a predetermined volume of the second liquid to the culture container.

11. A cell culture method that performs cell culture using, as a liquid feed device that feeds and discharges a liquid to and from a culture container arranged in a thermostat, a liquid feed device with a configuration comprising:

a first liquid containing unit that is configured to hold a first liquid;

a second liquid containing unit that is configured to hold a second liquid;

a pump connected between the first liquid containing unit and the second liquid containing unit;

a first supply pipe that is configured to supply the first liquid to the culture container through the pump;

a second supply pipe that is configured to supply the second liquid to the culture container with a pressurized liquid feed from the second liquid containing unit, a gas introducing valve that is configured to introduce gas into the second liquid containing unit, wherein the gas introducing valve includes: a first gas introducing valve connected via a first branch point to the first supply pipe, the first supply pipe having a first end thereof that is connected to the first liquid containing unit and having a second end thereof that is connected to the pump, and a second gas introducing valve connected between the pump and the second liquid containing unit, a first supply valve that is configured to open and close the first supply pipe between the pump and the culture container; and a second supply valve that is configured to open and close the second supply pipe between the second liquid containing unit and the culture container, wherein a control unit that is configured to: i) close the first supply valve, ii) open the first gas introducing valve, the second gas introducing valve, and the second supply valve, iii) activate the pump, so that the second liquid in the second liquid bottle is passed to the culture container through the second supply pipe, iv) close the second gas introducing valve and second supply valve, v) open the first supply valve, and vi) activate the pump, so that some amount of the second liquid is passed to the culture container.

* * * * *